(12) United States Patent
Elliott

(10) Patent No.: US 7,025,768 B2
(45) Date of Patent: Apr. 11, 2006

(54) SYSTEMS AND METHODS FOR ABLATION OF TISSUE

(75) Inventor: Christopher J. Elliott, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 143 days.

(21) Appl. No.: 10/431,178

(22) Filed: May 6, 2003

(65) Prior Publication Data

US 2004/0225286 A1    Nov. 11, 2004

(51) Int. Cl.
*A61B 18/12* (2006.01)

(52) U.S. Cl. .......................................... 606/45; 606/41
(58) Field of Classification Search ............. 606/41–52
See application file for complete search history.

(56) References Cited

U.S. PATENT DOCUMENTS

| | | | | |
|---|---|---|---|---|
| 5,336,222 | A * | 8/1994 | Durgin et al. ................. | 606/50 |
| 5,609,151 | A * | 3/1997 | Mulier et al. ................. | 600/373 |
| 5,645,082 | A * | 7/1997 | Sung et al. ................... | 128/897 |
| 5,881,732 | A * | 3/1999 | Sung et al. ................... | 128/898 |
| 5,888,546 | A * | 3/1999 | Ji et al. ........................ | 424/484 |
| 5,941,888 | A * | 8/1999 | Wallace et al. ............... | 606/108 |
| 6,048,333 | A * | 4/2000 | Lennox et al. ................ | 604/113 |
| 6,123,084 | A * | 9/2000 | Jandak et al. ................. | 128/898 |
| 6,162,216 | A * | 12/2000 | Guziak et al. ................ | 606/34 |
| 6,325,800 | B1 * | 12/2001 | Durgin et al. ................. | 606/45 |
| 6,327,505 | B1 * | 12/2001 | Medhkour et al. ............ | 607/99 |
| 6,371,972 | B1 * | 4/2002 | Wallace et al. ............... | 606/200 |
| 6,493,589 | B1 * | 12/2002 | Medhkour et al. ............ | 607/99 |
| 6,638,293 | B1 * | 10/2003 | Makower et al. ........... | 606/200 |
| 6,780,183 | B1 * | 8/2004 | Jimenez et al. ............... | 606/41 |
| 2001/0056281 | A1 * | 12/2001 | Wallace et al. ............. | 606/108 |
| 2002/0032486 | A1 | 3/2002 | Lazarovitz et al. | |
| 2002/0058962 | A1 * | 5/2002 | Wallace et al. ............. | 606/200 |
| 2002/0161342 | A1 * | 10/2002 | Rivelli et al. ................ | 604/273 |
| 2002/0165582 | A1 * | 11/2002 | Porter ......................... | 606/213 |

FOREIGN PATENT DOCUMENTS

| EP | 1 254 637 | 11/2002 |
|---|---|---|
| WO | WO 03/026525 | 4/2003 |

OTHER PUBLICATIONS

PCT International Search Report for PCT/US04/005554, Applicant: Scimed Life Systems, Inc., Forms PCT/ISA/210 and 220, dated Aug. 2, 2004 (6 pages).
PCT Written Opinion of the International Search Authority for PCT/US04/005554, Applicant: Scimed Life Systems, Inc., Form PCT/ISA/237, dated Aug. 2, 2004 (5 pages).

* cited by examiner

*Primary Examiner*—Roy D. Gibson
*Assistant Examiner*—Henry M Johnson, III
(74) *Attorney, Agent, or Firm*—Bingham McCutchen LLP

(57) ABSTRACT

A system for treating tissue includes a probe assembly having a cannula, a shaft, and one or more needle electrodes. The shaft has a distal end, a proximal end, and a lumen extending between the distal and proximal ends of the shaft, and is slidable within the lumen of the cannula. Each needle electrode has a lumen that may be placed in communication with a port at a proximal end of the probe assembly, and is configured to deliver an occlusive element to a site. The system may further include an embolization actuator for delivering the occlusive element. A method of treating tissue includes placing an electrode at a site of a treatment region, occluding at least a part of a vessel located adjacent the site by delivering an occlusion element from an electrode, and delivering ablation energy to the site while the vessel is at least partially occluded.

5 Claims, 5 Drawing Sheets

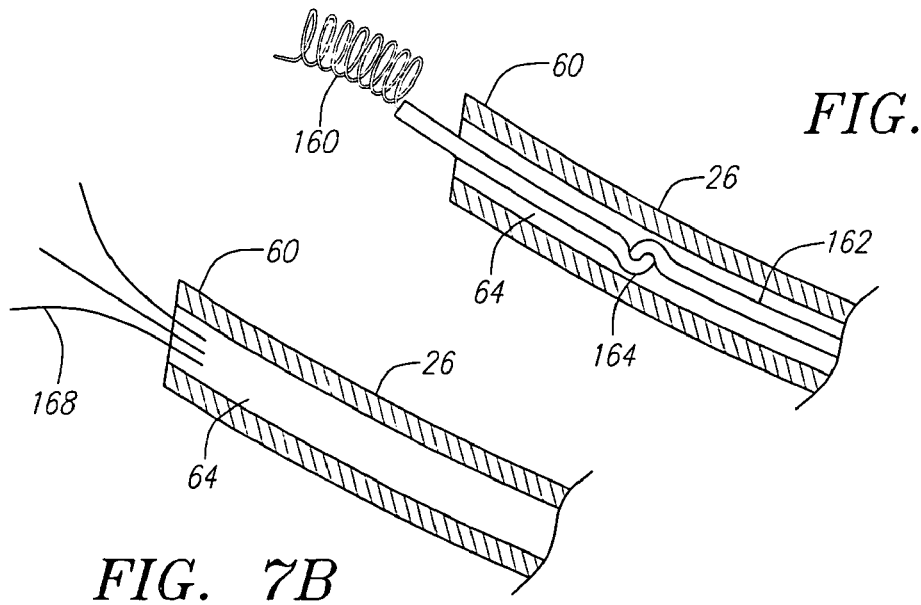
FIG. 7A
FIG. 7B
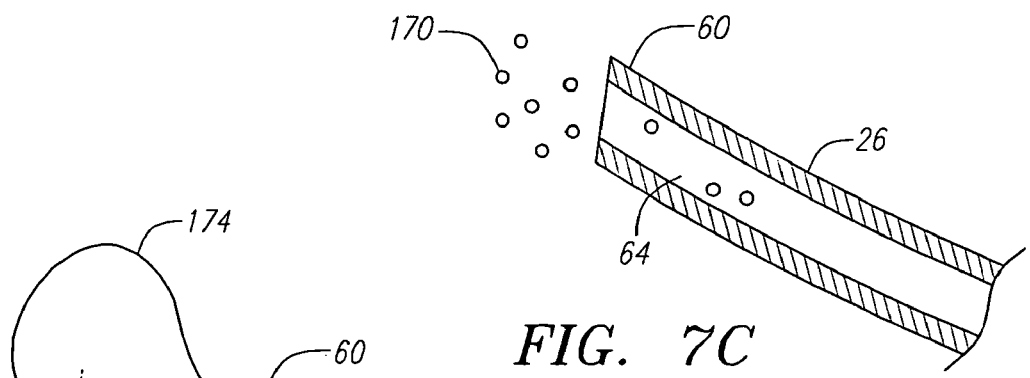
FIG. 7C
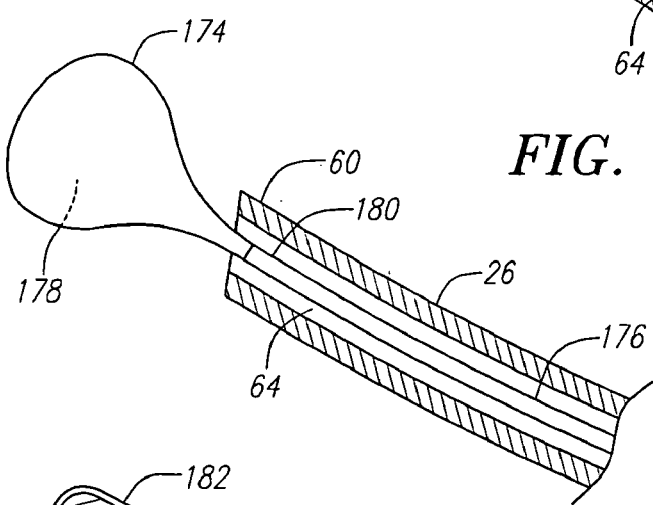
FIG. 7D
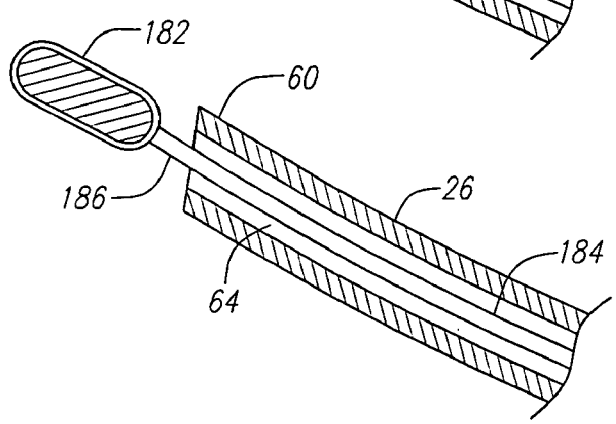
FIG. 7E

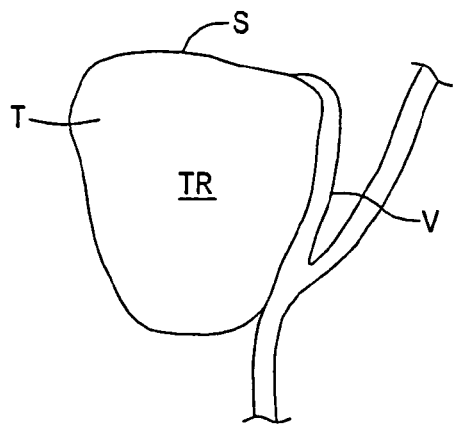 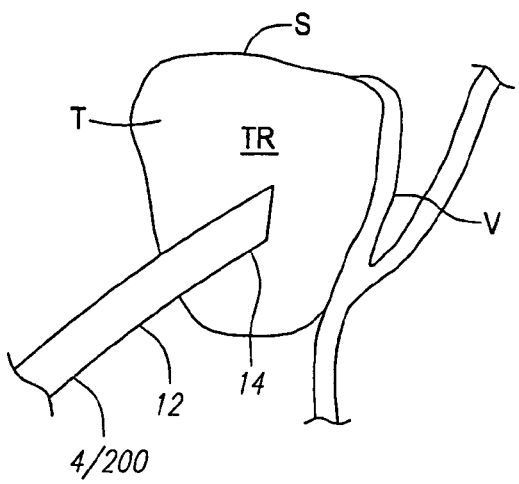
FIG. 9A          FIG. 9B
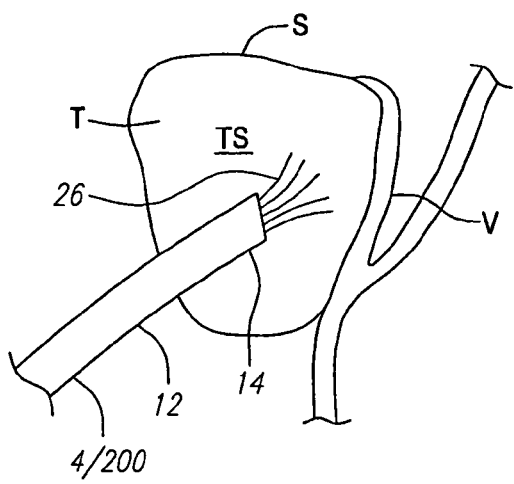 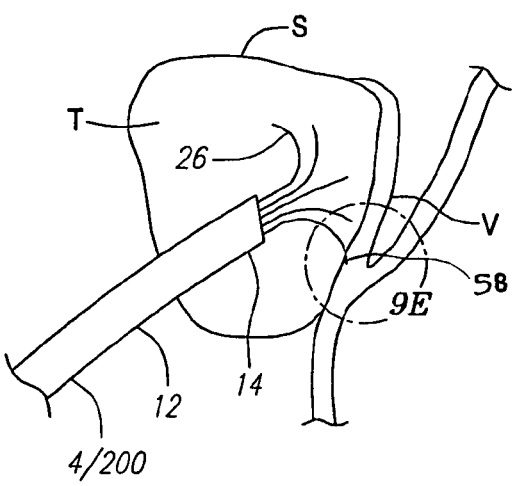
FIG. 9C          FIG. 9D
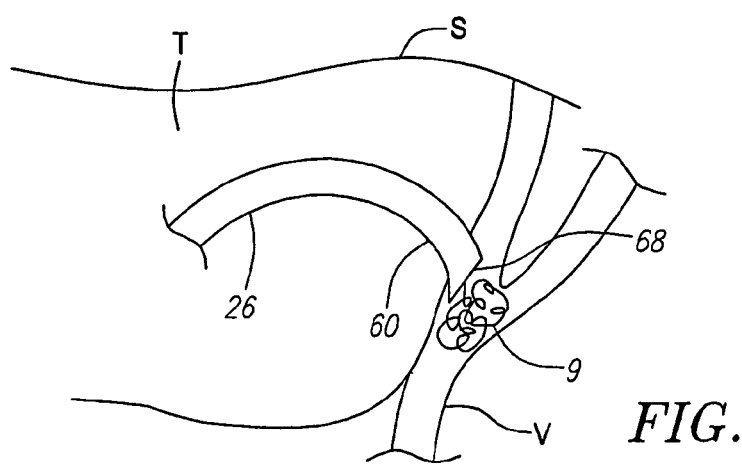
FIG. 9E

SYSTEMS AND METHODS FOR ABLATION OF TISSUE

BACKGROUND OF THE INVENTION

1. Field of the Invention

The field of the invention relates to medical devices, and more particularly, to systems and methods for ablating or otherwise treating tissue using electrical energy.

2. Background of the Invention

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction.

In particular, radio frequency ablation (RFA) may be used to treat patients with tissue anomalies, such as liver anomalies and many primary cancers, such as cancers of the stomach, bowel, pancreas, kidney and lung. RFA treatment involves destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of wire electrodes deployable from a cannula. Each of the wires includes a proximal end that is electrically coupled to a generator, and a distal end that may project from a distal end of the cannula. The wires are arranged in an array with the distal ends located generally radially and uniformly spaced apart from the catheter distal end. The wires may be energized in a monopolar or bipolar configuration to heat and necrose tissue within a precisely defined volumetric region of target tissue. Such devices may be used either in open surgical settings, in laparoscopic procedures, and/or in percutaneous interventions.

Generally, ablation therapy uses heat to kill tissue at a target site. The effective rate of tissue ablation is highly dependent on how much of the target tissue is heated to a therapeutic level. In certain situations, complete ablation of target tissue that is adjacent a vessel may be difficult or impossible to perform, since significant bloodflow may draw the produced heat away from the vessel wall, resulting in incomplete necrosis of the tissue surrounding the vessel. This phenomenon, which causes the tissue with greater blood flow to be heated less, and the tissue with lesser blood flow to be heated more, is known as the "heat sink" effect. It is believed that the heat sink effect is more pronounced for ablation of tissue adjacent large vessels that are more than 3 millimeters (mm) in diameter. Due to the increased vascularity of the liver, the heat sink effect may cause recurrence of liver tumors after a radio frequency ablation.

Accordingly, improved systems and methods for ablating tissue would be useful.

SUMMARY OF THE INVENTION

In accordance with a first aspect of the present invention, a system for treating tissue is provided that includes a probe assembly and/or an embolization actuator. The probe assembly includes a shaft carrying one or more electrodes. In one embodiment, the electrodes are needle electrodes. At least one of the needle electrodes has an electrode lumen. The shaft has a distal end, a proximal end, and a lumen extending between the distal and proximal ends of the shaft. In one embodiment, the probe assembly further includes a cannula having a distal end, a proximal end, and a lumen extending between the distal and proximal ends. The shaft may be slidable within the lumen of the cannula. In one embodiment, the shaft includes a plurality of delivery lumens. In this case, each needle electrode has a lumen that may be in fluid communication with the delivery lumen of the shaft. In another embodiment, the shaft includes a single lumen, and each needle electrode may extend proximally through the entire length of the shaft within the shaft lumen.

The needle electrodes may be used to ablate tissue and/or deliver an occlusion element to a site, such as a vessel. By way of non-limiting examples, the occlusion element may include an embolic coil, liquid embolic, an occlusion balloon, embolic particles, and a filter. In one embodiment, the needle electrodes have sharp distal tips that allow the tubular electrodes to penetrate tissue, such as a wall of a vessel. The probe assembly may further include one or more radio-opaque markers secured to one or all of the needle electrodes.

The embolization actuator may include a variety of devices, the type of which depends on the type of occlusion element used. By way of non-limiting examples, for delivery of embolic coil, the embolization actuator may include an elongate member, such as a guidewire for distally advancing the embolic coil within the electrode lumen. For delivery of liquid embolic, the embolization actuator may include a syringe or a pump for delivering the liquid embolic. For delivery of embolic particles, the embolization actuator may include a plunger. Alternatively, if the embolic particles are delivered within a solution, the embolization actuator may include a syringe, a pump, and/or the solution. Other types of embolization actuator are also described.

The probe assembly may also include an indexer, or a handle member having indexing capability, that is secured to the proximal end of the shaft. The handle allows a user to select which of the needle electrodes is used to deliver the occlusion element. In one embodiment, the handle member may include a port and may be rotated about a longitudinal axis of the tubular member such that the port is in fluid communication with one of the delivery lumens and/or the electrode lumens. The handle member and/or the shaft may include a marker to indicate an orientation or a position of the handle relative to the shaft. One or more occlusion elements may be inserted into the port of the handle, and distally advanced through the lumen of the tubular section and through the lumen of the needle electrode to a site.

In another embodiment, the probe assembly includes an indexer that is placed within the lumen of the shaft. The indexer includes a lumen and may be rotated about a longitudinal axis of the tubular member such that the lumen of the indexer may be in fluid communication with the lumen of one of the needle electrodes. The indexer and/or the shaft may include a marker to indicate an orientation or a position of the indexer relative to the shaft. One or more occlusion elements may be inserted into the lumen of the indexer and distally advanced through the lumen of the needle electrode to a site.

In accordance with another aspect of the invention, a medical probe assembly includes an elongated shaft, a plurality of tissue penetrating elements carried by the elongated shaft, a port carried by the elongated shaft, and an indexer carried by the elongated shaft. Each of the plurality of tissue penetrating elements includes a lumen. The indexer is configured for selectively placing the port in communication with the lumen of one of the tissue penetrating elements.

In accordance with yet another aspect of the invention, a system of occluding blood flow includes a probe assembly having an inlet and a plurality of outlet ports, an indexer configured for selectively placing the inlet port in communication with one of the outlet ports, and an embolization actuator for delivering an occlusion element through the inlet port.

In accordance with another aspect of the invention, a tissue ablation system includes a probe assembly having one or more ablation electrodes, and an embolization actuator. The one or more electrodes each has a lumen. The embolization actuator is configured to be in communication with at least one of the electrode lumens.

In accordance with another aspect of the present invention, a method is provided for treating tissue at a treatment region. The method of treating tissue includes inserting an occlusion electrode through a wall of the vessel, delivering an occlusion element from the electrode into a lumen of the vessel to at least partially occlude the flow of blood through the vessel, and delivering ablation energy to the tissue while the vessel is at least partially occluded.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

FIGS. 7A–7E are partial cross-sectional views of the distal end of one of the needle electrodes, particularly showing variations of usage of the needle electrode;

FIGS. 9A–9E illustrate cross-sectional views of one preferred method of using the tissue treatment system of FIG. 1 to treat target tissue;

DETAILED DESCRIPTION OF THE PREFERRED EMBODIMENTS

Figure 1:
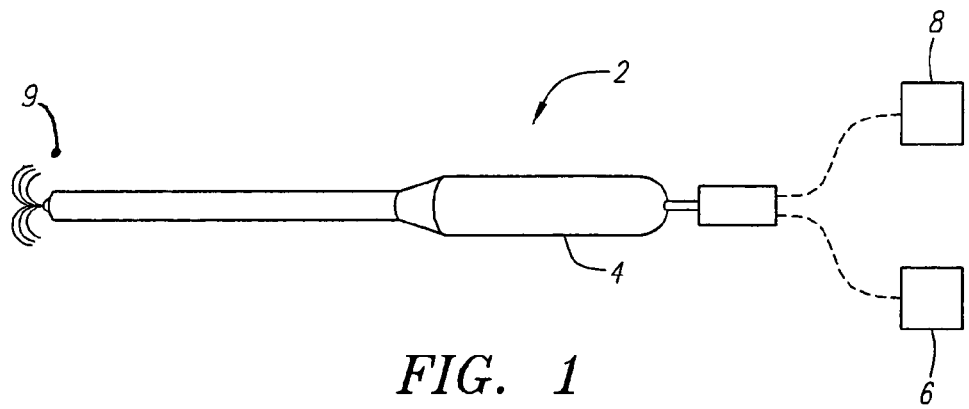
FIG. 1 is a block diagram of a tissue ablation system constructed in accordance with an embodiment of the present invention.

FIG. 1 illustrates a tissue ablation system 2 constructed in accordance with a preferred embodiment of the present inventions. The tissue ablation system 2 generally comprises a probe assembly 4 configured for introduction into the body of a patient for ablative treatment of target tissue. The tissue ablation system 2 also includes a radio frequency (RF) generator 6 configured for supplying RF energy to the probe assembly 4 in a controlled manner, and an embolization actuator 8 for delivering occlusive element(s) 9 to a site, such as a blood vessel, so that a more efficient and effective ablation treatment is effected.

Figure 2:
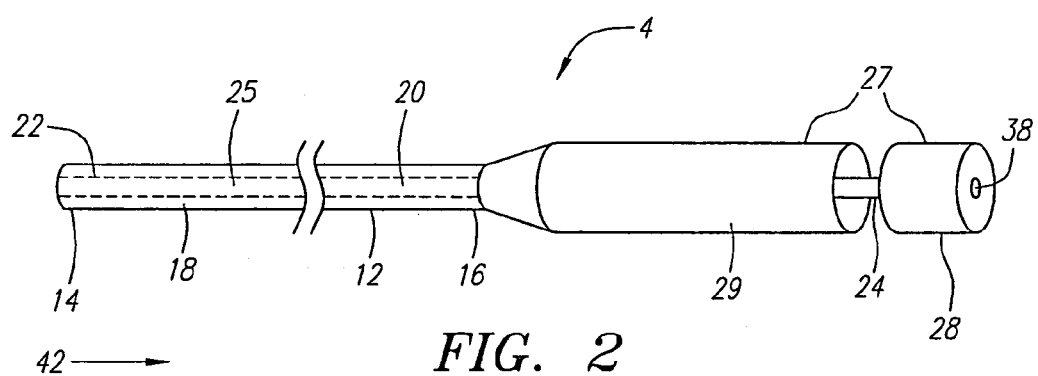
FIG. 2 is a side view of an ablation probe assembly used in the tissue treatment system of FIG. 1, wherein a needle electrode array is particularly shown retracted.
Figure 3:
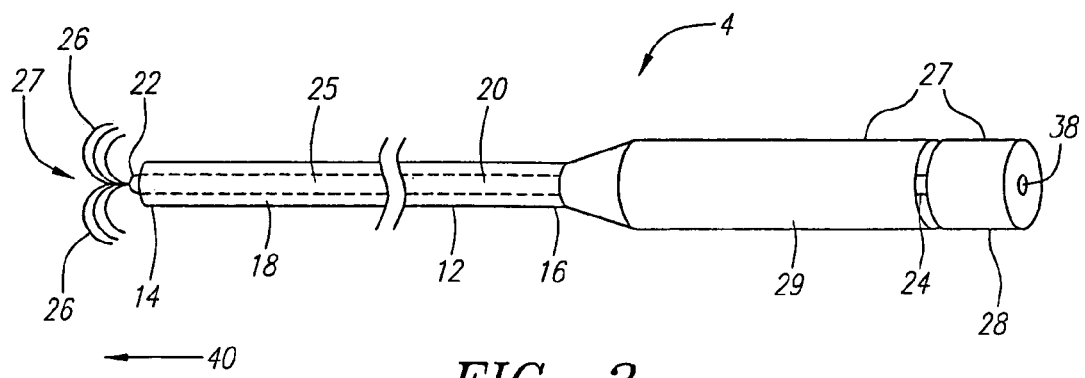
FIG. 3 is a side view of an ablation probe assembly used in the tissue treatment system of FIG. 1, wherein the needle electrode array is particularly shown deployed.

Referring specifically now to FIGS. 2 and 3, the probe assembly 4 generally comprises an elongated cannula 12, a shaft 20 slidably disposed within the cannula 12, and a plurality of electrodes 26 carried by the shaft 20. The cannula 12 has a distal end 14, a proximal end 16, and a central lumen 18 extending through the cannula 12 between the distal end 14 and the proximal end 16. As will be described in further detail below, the cannula 12 may be rigid, semi-rigid, or flexible depending upon the designed means for introducing the cannula 12 to the target tissue. The cannula 12 is composed of a suitable material, such as plastic, metal or the like, and has a suitable length, typically in the range from 5 cm to 30 cm, preferably from 10 cm to 20 cm. If composed of an electrically conductive material, the cannula 12 is preferably covered with an insulative material. The cannula 12 has an outside diameter consistent with its intended use, typically being from 1 mm to 5 mm, usually from 1.3 mm to 4 mm. The cannula 12 has an inner diameter in the range from 0.7 mm to 4 mm, preferably from 1 mm to 3.5 mm. The cannula 12 may also have other outside and inner diameters.

The shaft 20, which may be a surgical probe shaft, comprises a distal end 22 and a proximal end 24. Like the cannula 12, the shaft 20 is composed of a suitable material, such as plastic, metal or the like. It can be appreciated that longitudinal translation of the shaft 20 relative to the cannula 12 in a distal direction 40 deploys the needle electrodes 26 from the distal end 14 of the cannula 12 (FIG. 3), and longitudinal translation of the shaft 20 relative to the cannula 12 in a proximal direction 42 retracts the shaft 20 and the needle electrodes 26 into the distal end 14 of the cannula 12 (FIG. 2).

Figure 4:
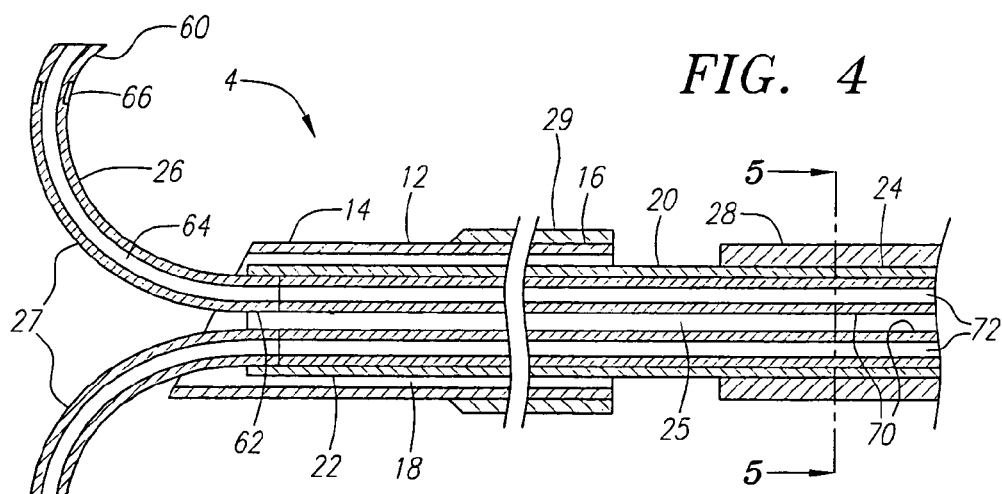
FIG. 4 is a partial cross-sectional side view of the probe assembly of FIG. 3.
Figure 5:
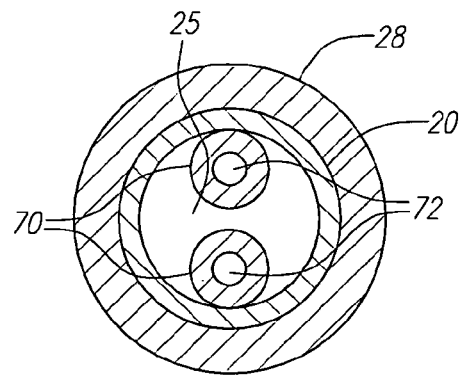
FIG. 5 is a cross-sectional end view of the proximal end of the probe assembly of FIG. 4.

Referring to FIGS. 4 and 5, the shaft 20 further comprises a plurality of delivery lumens 72 extending from its proximal end 24 to its distal end 22. In one embodiment, each electrode 26 is a needle electrode, which resembles the shape of a needle or wire. However, the electrodes 26 may also have other shapes as well. As will be described in further detail below, the lumens 72 provide a means for delivering one or more occlusive elements from the needle electrodes 26. In the illustrated embodiment, the lumens 72 are composed of separate tubes 70 that are disposed within a main lumen 25 of the shaft 20. Alternatively, the lumens 72 can be formed within the shaft 20 itself, e.g., by forming the shaft 20 and lumens 72 from a single extrusion.

In the illustrated embodiment, the proximal ends 62 of the electrodes 26 are secured to the distal end 22 of the shaft 20, e.g., by a weld, brazing, a glue, or other suitable adhesive, depending on the materials from which the electrode 26 and the shaft 20 are made. Each of the electrodes 26 comprises a lumen 64 that is in communication with a respective lumen 72 of the shaft 20, and an opening or outlet port 68 from which an occlusive element 9 may exit, as will be described in further detail below.

Each of the individual needle electrodes 26 is in the form of a small diameter metal element, which can penetrate into tissue as it is advanced from a target site within the target region. When deployed from the cannula 12, the array 27 of needle electrodes 26 is placed in a three-dimensional configuration that usually defines a generally ellipsoidal or spherical volume having a periphery with a maximum radius in the range from 0.5 to 3 cm. The needle electrodes 26 are resilient and pre-shaped to assume a desired configuration when advanced into tissue. In the illustrated embodiment, the needle electrodes 26 diverge radially outwardly from the cannula 12 in a uniform pattern, i.e., with the spacing between adjacent needle electrodes 26 diverging in a substantially uniform and/or symmetric pattern. In the illustrated embodiment, the needle electrodes 26 also evert proximally, so that they face partially or fully in the proximal direction when fully deployed. In exemplary embodiments, pairs of adjacent needle electrodes 26 can be spaced from each other in similar or identical, repeated patterns and can be symmetrically positioned about an axis of the shaft 20. It will be appreciated that a wide variety of particular patterns can be provided to uniformly cover the region to be treated. It should be noted that although a total of six needle electrodes 26 are illustrated in FIG. 3, additional needle electrodes 26 can be added in the spaces between the illustrated needle electrodes 26, with the maximum number of needle electrodes 26 determined by the electrode width and total circumferential distance available (i.e., the needle electrodes 26 could be tightly packed). It should be noted that the shape and spacing of the needle electrodes 26 should not be limited to that described previously, and that the needle electrodes 26 may have other pre-formed shapes and may be spaced from each other in a non-uniform pattern.

Each individual needle electrode 26 is preferably composed of a single tubular wire that may be composed from a variety of elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The needle electrode 26 may also be made from any of a wide variety of stainless steels. The needle electrode 26 may also include the Platinum Group metals, especially platinum, rhodium, palladium, rhenium, as well as tungsten, gold, silver, tantalum, and alloys of these metals. These metals are largely biologically inert. They also have significant radiopacity to allow the needle electrodes 26 to be visualized in-situ, and their alloys may be tailored to accomplish an appropriate blend of flexibility and stiffness. They may be coated onto the needle electrodes 26 or be mixed with another material used for construction of the needle electrodes 26. The needle electrodes 26 may have circular or non-circular cross-sections, but preferably have rectilinear cross-sections. In this manner, the needle electrodes 26 are generally stiffer in the transverse direction and more flexible in the radial direction. By increasing transverse stiffness, proper circumferential alignment of the needle electrodes 26 within the lumen 18 of the cannula 12 is enhanced. Exemplary needle electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm.

The distal ends 66 of the needle electrodes 26 may be honed or sharpened to facilitate their ability to penetrate tissue. The distal ends 66 of these needle electrodes 26 may be hardened using conventional heat treatment or other metallurgical processes. They may be partially covered with insulation, although they will be at least partially free from insulation over their distal portions.

The needle electrodes 26 are electrically coupled to the distal end 22 of the shaft 20. This can be accomplished in a variety of manners, but in the illustrated embodiment, the electrodes 26 are coupled to the distal end 22 of the shaft 20 via intermediate electrical conductors, such as wires (not shown), that can be disposed within a wall, main lumen 25 or delivery lumens 72 of the shaft 20. Alternatively, the shaft 20 and any component between the shaft 20 and the needle electrodes 26, are composed of an electrically conductive material, such as stainless steel, and may therefore conveniently serve as intermediate electrical conductors. Even more alternatively, the needle electrodes 26 may proximally extend the entire distance of the shaft 20, in which case, the delivery lumens 72 may not be necessary.

Each electrode 26 may also include a radio-opaque marker 66 and/or a sensor (not shown) carried at the distal end 60 of the electrode 26. The sensor may be used to sense a characteristic, such as the impedance or the temperature, of tissue being ablated. In one embodiment, each electrode 26 may have a radio-opaque marker having a different configuration (i.e., shape, geometry, size) that is different from others. This allows identification of the electrodes 26.

In the illustrated embodiment, the RF current is delivered to the electrode array 27 in a monopolar fashion, which means that current will pass from the electrode array 27, which is configured to concentrate the energy flux in order to have an injurious effect on the surrounding tissue, and a dispersive electrode (not shown), which is located remotely from the electrode array 27 and has a sufficiently large area (typically 130 $cm^2$ for an adult), so that the current density is low and non-injurious to surrounding tissue. In the illustrated embodiment, the dispersive electrode may be attached externally to the patient, e.g., using a contact pad placed on the patient's flank. In a monopolar arrangement, the needle electrodes 26 are bundled together with their proximal portions having only a single layer of insulation over the cannula 12.

Alternatively, the RF current is delivered to the electrode array 27 in a bipolar fashion, which means that current will pass between two electrodes ("positive" and "negative" electrodes). In a bipolar arrangement, the positive and negative needle electrodes will be insulated from each other in any regions where they would or could be in contact with each other during the power delivery phase.

Returning to FIGS. 2 and 3, the probe assembly 4 further comprises a handle assembly 27, which includes a member 28 mounted to the proximal end 24 of the shaft 20, and an handle sleeve 29 mounted to the proximal end 16 of the cannula 12. The handle member 28 is slidably engaged with the handle sleeve 29 (and the cannula 20). The handle member 28 also comprises an electrical connector 38 in which the proximal ends of the needle electrodes 26 (or alternatively, intermediate conductors) are coupled. The handles member 28 and the handle sleeve 29 can be composed of any suitable rigid material, such as, e.g., metal, plastic, or the like.

Figure 6A:
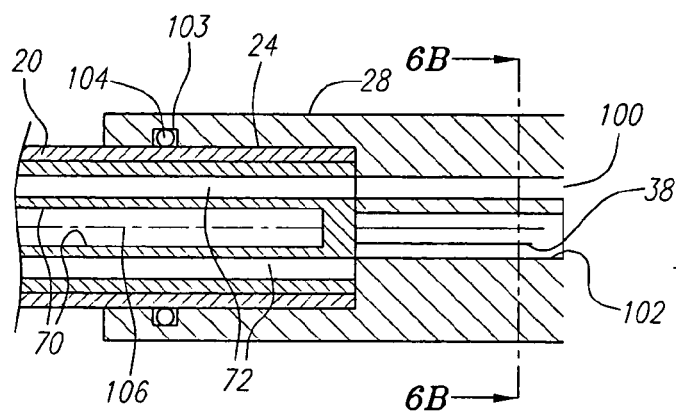
FIGS. 6A and 6B are cross-sectional side and end views, respectively, of a handle of the probe assembly of FIG. 2.
Figure 6B:
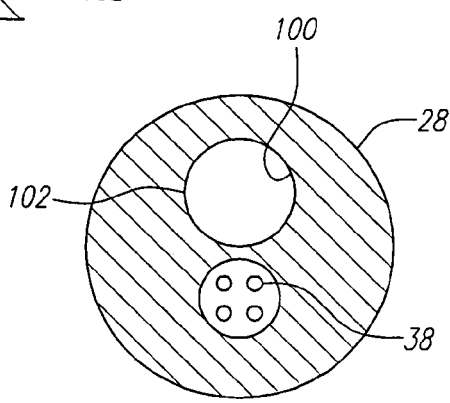

FIGS. 6A and 6B, the handle member 28 includes a delivery or inlet port 100, which is configured to be in fluid communication with one of the delivery lumens 72 for delivery of the occlusive element 9. In this case, the electrode lumen 64 would be in indirect fluid communication with the delivery port 100. Alternatively, if the needle electrodes 26 proximally extend the entire distance of the shaft 20, the delivery port 100 may be configured to be in direct fluid communication with one of the electrode lumens 64. In the illustrated embodiment, the handle member 28 has a recess 103 that is adapted to mate with a protrusion 104 of the shaft 20, thereby rotatably securing the handle member 28 to the proximal end 24 of the shaft 20. In this case, a user may rotate the handle member 28 about a longitudinal axis 106 to selectively choose which of the delivery lumens 72, and therefore, which of the lumens 64 of the electrodes 26, with which the port 100 is in communication. As such, the handle member 28 serves as an indexer for selecting one of the electrodes 26. The handle member 28 also includes an electrical port 102 housing the electrical connector 38. Alternatively, the electrical connector 38 may be located on the proximal end 24 of the shaft 20 distal to the handle member 28. In this case, the electrical port 102 of the handle member 28 may not be necessary. Optionally, a marker (not shown) may be placed on the handle member 28 and/or on the proximal end 24 of the shaft 20 for indicating a rotational orientation or a position of the handle member 28 relative to the shaft 20 (and the electrodes 26) during use.

In another embodiment, instead of coupling the handle member 28 to the shaft 20 using the recess 103 and the protrusion 104, the handle member 28 may be configured to slidably engage the shaft 20. In this case, the shaft 20 may include a plurality of slots disposed on the exterior surface of the shaft 20, and the handle member 28 may include an indexing key that can mate with the respective slots on the shaft 20 as the handle member 28 is axially advanced relative to the shaft 20. Such indexing feature allows better alignment of the delivery port 100 with a desired shaft lumen 72. Angle indexing devices that may be used include those described in U.S. patent application Ser. No. 10/317,796, entitled "Angle Indexer For Medical Devices", the entire disclosure of which is expressly incorporated by reference herein. In another embodiment, the handle member 28 may also include a locking mechanism (not shown) to temporarily lock against the shaft 20 to provide a more stable indexing. For example, the locking mechanism may include an axially-sliding clutch assembly that is slidable along an axis of the shaft 20 to thereby secure the handle member 28 against the shaft 20. Other securing devices known in the art may also be used.

Referring back to FIG. 1, the RF generator 6 is electrically connected to the electrical connector 38, which as previously described, may be directly or indirectly electrically coupled to the electrode array 27. The RF generator 6 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as RadioTherapeutics of San Jose, Calif., who markets these power supplies under the trademarks RF2000 (100 W) and RF3000 (200 W).

Further details regarding needle electrode array-type probe arrangements are disclosed in U.S. Pat. No. 6,379,353, entitled "Apparatus and Method for Treating Tissue with Multiple Electrodes," which is hereby expressly incorporated herein by reference.

As previously described, the system 2 is designed to deliver one or more occlusive elements 9 within a blood vessel. The specific design of the needle electrodes 26 (e.g., the cross-section of the needle electrodes 26) and the embolization actuator 8 will depend upon the occlusive elements 8 that are to be delivered within the blood vessel. FIGS. 7A–7E show examples of the types of embolization actuators 8 and occlusion elements 9 that may be delivered by a needle electrode 26.

FIG. 7A shows the needle electrode 26 delivering an embolic coil 160 (the occlusive element 9) from the outlet port 68 to a site. The embolic coil 160 may be detachably coupled to an elongate member 162, such as a pusher wire, a core wire, or a guide wire by a joint 164. In this case, the embolization actuator 8 includes the elongate member 162, which may be used to distally advance the embolic coil 160 within one of the electrode lumens 64. The embolic coil 160 may have a variety of primary shapes, secondary shapes, and/or tertiary shapes. Embolic coil designs, and methods of making such, are described in U.S. Pat. No. 6,322,576B1 to Wallace et al., the entirety of which is incorporated by reference herein. In one embodiment, the embolic coil 160 is stretched into a low profile when resided within the lumen 64 of the electrode 26, and assumes a three-dimensional configuration when outside the lumen 64. The embolic coil 160 may be detachable by electrolytic means such as described in U.S. Pat. Nos. 5,234,437, 5,250,071, 5,261,916, 5,304,195, 5,312,415, and 5,350,397, the disclosures of which are expressly incorporated by reference herein. It will be appreciated that mechanical joints, and other types of detachable joints known in the art for placing occlusive elements in a site may alternatively be used to couple the occlusion coil 160 to the elongate member 162. Examples of such mechanical joints may be found in U.S. Pat. No. 5,234,437, to Sepetka, U.S. Pat. No. 5,250,071 to Palermo, U.S. Pat. No. 5,261,916, to Engelson, U.S. Pat. No. 5,304,195, to Twyford et al., U.S. Pat. No. 5,312,415, to Palermo, and U.S. Pat. No. 5,350,397, to Palermo et al, the disclosures of which are expressly incorporated herein by reference.

FIG. 7B shows the needle electrode 26 delivering liquid embolic 168 (the occlusive element 9) to a site. In the illustrated embodiment, the liquid embolic 168 is delivered by the lumen 64 of the needle electrode 26 out through the outlet port 68. Alternatively, the liquid embolic 168 may be delivered by one or more tubular delivery members that are positioned within the lumen 64 of the electrode 26. Examples of liquid embolic that may be used are described in U.S. Pat. Nos. 6,139,520 and 6,152,943, the entireties of which are expressly incorporated herein by reference. U.S. Pat. No. 6,139,520 discloses a cross linked polysaccharide fiber formed by combining a first liquid including polysaccharide and a second liquid including an ionic cross linking agent. U.S. Pat. No. 6,152,943 discloses a polymer formed by two components. Delivery of the liquid embolic 168 may be accomplished by using the embolization actuator 8, which in this case may be a syringe, a pump, or other devices known for delivering fluid. Particularly, the embolization actuator 8 may be used to apply pressure within the shaft lumen 72 and/or the lumen 64 of the needle electrode 26 to assist delivery of the liquid embolic 168. If the handle member 28 is used, the embolization actuator 8 may be coupled to the delivery port 100 of the handle member 28. For example, the embolization actuator may be coupled to the handle member 28 so that the embolization actuator 8 can be placed in communication with one of the needle lumen 64 or one of the shaft lumens 72.

FIG. 7C shows the needle electrode 26 delivering embolic particles 170 (the occlusive element 9) to a site. In the illustrated embodiment, the embolic particles 170 are delivered by the lumen 64 of the needle electrode 26 out through the outlet port 68. The embolization actuator 8, which in this case may include a plunger, may be used to distally advance the embolic particles 170 within one of the electrode lumens 64. Alternatively, the embolic particles 170 may be delivered by another tubular delivery member that is positioned within the lumen 64 of the needle electrode 26. The embolic particles 170 may also be delivered in a liquid solution, such as saline. In this cause, the embolization actuator 8 may include a syringe or a pump for delivering the liquid solution, as similarly-discussed previously with reference to FIG. 7B. An example of the type of embolic particles 90 that may be use is the Contour®-PVA particles, available from the Boston Scientific Corporation. The embolic particles 170 may have a wide range of sizes. The Contour-PVA particles have particle sizes that range from 45–150 to 1000–1180 microns. Embolic particles 170 having other sizes may also be used, depending on the particular application. In one embodiment, the embolic particles 170 are spherical in shape. In alternative embodiments, the embolic particles 170 may have other geometric shapes and/or irregular shapes.

FIG. 7D shows the needle electrode 26 delivering an occlusion balloon 174 (the occlusive element 9) to a site. The balloon 174 may be detachably coupled (for permanent occlusion of a site) or non-detachably coupled (for temporary occlusion of a site) to at the distal end 180 of an inflation tube 176 disposed within the electrode lumen 64. Alternatively, the corresponding electrode lumen 64 and shaft lumen 72 may acts as the inflation tube. The inflation tube 176 delivers an inflation medium to an interior 178 of the balloon 174 for inflation of the balloon 174. In this case, the embolization actuator 8 may include a pump, a syringe, or other medium delivery device for delivering the inflation medium to the interior 178 of the balloon 174. The balloon 174 is preferably made of a thermoplastic or elastomeric materials, such as polyimide (kapton), polyester, silicone rubber, nylon, mylar, polyethelene, or polyvinyl chloride. However, other elastic materials known in the art may also be used for construction of the balloon 174. Medical balloons have been described in U.S. Pat. No. 5,925,083, the entirety of which is hereby incorporated by reference. It should be noted that the shape of the balloon 94 is not necessarily limited to that illustrated in the figure. Other designed shapes may also be used. Furthermore, the size of the balloon 174 may vary, depending on the particular application. For example, a relatively larger balloon 174 may be used to occlude a large vessel, while a smaller balloon 94 may be used to occlude a smaller vessel.

FIG. 7E shows the needle electrode 26 delivering to a site a nonporous filter 182 (the occlusive element 9) that is secured to a wire 184 at a distal end 186. In this case, the embolization actuator 8 includes the wire 184, which may be used to distally advance the filter 182 within one of the electrode lumens 64 out through the corresponding outlet port 68. The filter 182 may be used to slow blood flow in a vessel. The filter 182 may be made of a variety of materials, such as nylon, polymer, plastics, and/or metals. In one embodiment, the filter 182 is made at least partially from Nitinol, which allows the filter 182 to unfold itself to form a membrane when outside the lumen 64 of the needle electrode 26, and be stretched or folded into a low profile when resided within the lumen 64. Deployment of the filter 182 may be accomplished by distally advancing the wire 184 that is placed within the lumen 64 of the needle electrode 26.

It should be noted that the occlusion element 9 that may be delivered by the needle electrode 26 should not be limited to the examples discussed previously, and that other occlusion elements may also be used so long as they are capable of at least partially occluding a site, such as a vessel.

Figure 8A:
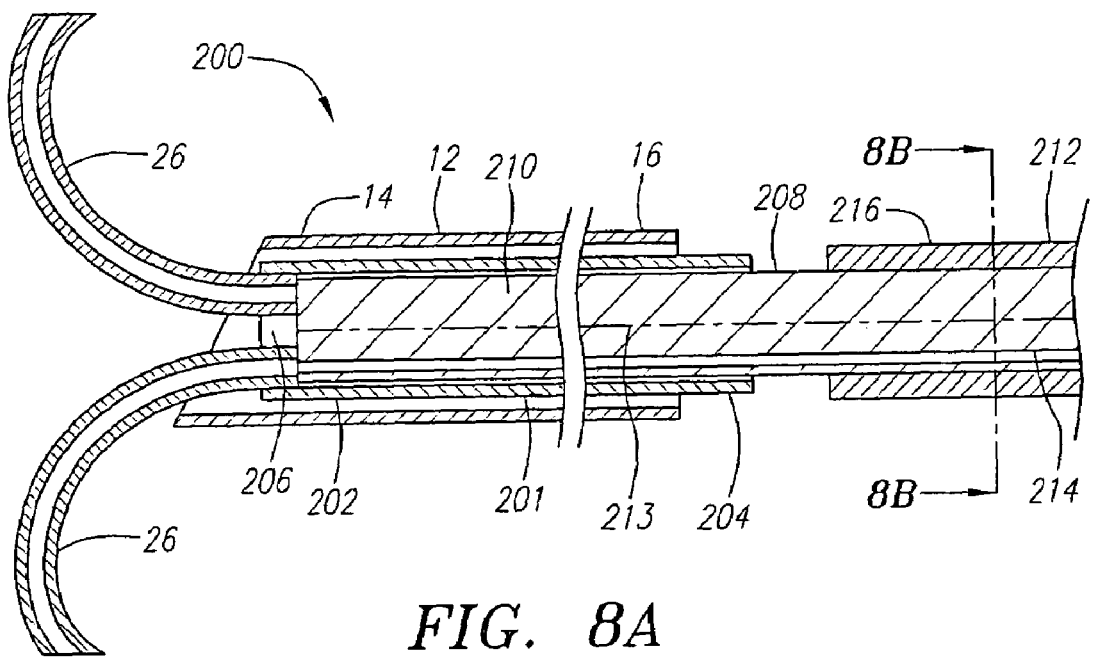
FIG. 8A is a partial cross-sectional side view of another ablation probe assembly that can be used in the ablation system of FIG. 1.
Figure 8B:
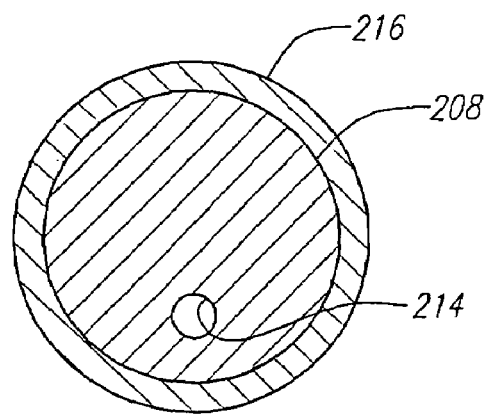
FIG. 8B is a cross-sectional end view of the probe assembly of FIG. 8A.

FIGS. 8A and 8B shows another probe assembly 200 that can be used in the previously described system 2. The probe assembly 200 is similar to the previously described probe assembly 4, with the exception that it comprises a different means for indexing which of the needle electrodes 26 will be used to embolize the blood vessel. Specifically, the probe assembly 200 includes a shaft 201 having a distal end 202, a proximal end 204, and a lumen 206 extending between the distal and proximal ends 202 and 204. The electrodes 26 are carried on the distal end 202 of the shaft 201, and may be deployed by distally advancing the shaft 201 relative to the cannula 12. The probe assembly 200 also includes an indexer 208 having a distal end 210, a proximal end 212, and a lumen 214 extending between the distal and proximal ends 210 and 212. The indexer 208 is configured to be placed within the lumen 206 of the shaft 201, and may be rotated about a longitudinal axis 213 of the shaft 201. In particular, the indexer 208 may be rotated such that the lumen 214 of the indexer 208 is in communication with one of the lumens 64 of the electrodes 26. A handle 216 that secures to the proximal end 212 of the indexer 208 may be provided to facilitate manipulation of the indexer 208. Optionally, a marker (not shown) may be placed on the handle 216 and/or on the proximal end 212 of the indexer 208 for indicating a rotational orientation or a position of the handle 216 relative to the shaft 201 (and the electrodes 26) during use.

Referring now to FIGS. 9A–9E, the operation of the tissue ablation system 2 is described in treating a treatment region TR within tissue T located beneath the skin or an organ surface S of a patient. The tissue T prior to treatment is shown in FIG. 9A. The cannula 12 is first introduced within the treatment region TR, so that the distal end 14 of the cannula 12 is located at the target site TS, as shown in FIG. 9B. This can be accomplished using any one of a variety of techniques. In some cases, the cannula 12 and shaft 20 may be introduced to the target site TS percutaneously directly through the patient's skin or through an open surgical incision. In this case, the cannula 12 may have a sharpened tip, e.g., in the form of a needle, to facilitate introduction to the target site TS. In such cases, it is desirable that the cannula 12 be sufficiently rigid, i.e., have a sufficient column strength, so that it can be accurately advanced through tissue T. In other cases, the cannula 12 may be introduced using an internal stylet that is subsequently exchanged for the shaft 20 and electrode array 27. In this latter case, the cannula 12 can be relatively flexible, since the initial column strength will be provided by the stylet. More alternatively, a component or element may be provided for introducing the cannula 12 to the target site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 12 and shaft 20 can then be introduced through the sheath lumen, so that the distal end 14 of the cannula 12 advances from the sheath to the target site TS.

After the cannula 12 is properly placed, the shaft 20 is distally advanced to deploy the electrode array 27 radially outward from the distal end 14 of the cannula 12, as shown in FIG. 9C. The shaft 20 will be advanced sufficiently, so that the electrode array 27 fully everts in order to circumscribe substantially the entire treatment region TR, as shown in FIG. 9D. Alternatively, the needle electrodes 26 may be only partially deployed or deployed incrementally in stages during a procedure.

As shown in FIG. 9E, the needle electrodes 26 are deployed such that one of the needle electrodes 26 (the occlusion electrode) penetrates a wall of a vessel V adjacent the treatment region TR. The radio-opaque markers 66 carried at the distal ends 60 of the needle electrodes 26 and/or the markers (if they are provided) may be used to assist deploying one of the needle electrodes 26 such that its tip penetrates the wall of the vessel V. If the tip 58 of one of the needle electrodes 26 is unable to reach the vessel V, the needle electrodes 26 may be retracted and re-deployed at different orientation by torsionally rotating the probe assembly 4 (or 200). Alternatively, the probe assembly 4 (or 200) may be removed from the patient, and re-inserted into the patient at a different location such that deployment of the needle electrodes 26 may allow one of the needle electrodes 26 to reach the vessel V. In a further alternative, the system 2 may further include a stylet that can be inserted through the delivery port 100 of the handle member 28 (if one is provided), the delivery lumen 72, and then through the lumen 64 of one of the electrodes 26. The stylet serves as an extension of the needle electrode 26, and may be used to penetrate the wall of the vessel V. The stylet may have a substantially rectilinear shape, or alternatively, may have a variety of pre-formed shapes. The stylet may be made from any of the materials described previously with reference to the needle electrodes 26.

After the distal end 66 of one of the electrode 26 is placed within the lumen of the vessel V, the delivery port 100 is aligned with the delivery lumen 72 corresponding to the lumen 64 of the electrode 26 that has been placed within the vessel V. Specifically, if the handle member 28 is used, the handle member 28 may be rotated about a longitudinal axis of the shaft 20 to align the port 100 with one of the delivery lumens 72 or with one of the electrode lumens 64, which corresponds to the electrode 26 placed within the lumen of the vessel V. If the indexer 208 is used, the indexer 208 may be rotated about a longitudinal axis of the shaft 201 to align the lumen 214 of the indexer 208 with the electrode lumens 64 which corresponds to the electrode 26 placed within the lumen of the vessel V. A marker located at the handle member 28 (or the indexer 208) and/or the shaft 20 (or 201) may be used to indicate the orientation or position of the handle member 28 (or the indexer 208) relative to the shaft 20 (or 201). A contrast agent may be delivered through the port 100 to verify that the position of the port 100 corresponds to the desired needle electrode 26. Radio-opaque markers 66 (if they are provided) carried at the distal ends of the electrodes 26 may also be used to identify the desired electrode 26.

After the desired electrode 26 has been verified, the RF generator 6 is then connected to the probe assembly 4 (or 200) via the electrical connector 38. If the system 2 includes the embolization actuator as discussed previously, the embolization actuator may also be connected to the delivery port 100 of the handle member 28 for delivery of the occlusion element 9 through the delivery port 100, through the indexed shaft lumen 72, and then out through the lumen 64 of the electrode 26 (FIG. 9E). If the alternative probe assembly 200 is instead used, the occlusion element 9 is delivered through the lumen 214 of the indexer 208, and then out through the lumen 64 of the electrode 26 into the lumen of the vessel V. Thus, it can be appreciated that the electrode 26 serves as a delivery catheter that delivers the occlusion element 9 to the lumen of the vessel V in a manner similar to any of the known conventional methods.

The insertion of the occlusion element into the vessel V reduces or prevents substantial blood flow through the vessel V, thereby reducing the possibility that bloodflow may draw produced heat away from the vessel wall during ablation of the treatment region TR. Any of the occlusion elements discussed previously may be used. The occlusion of the vessel V may or may not be permanent. For example, one or more embolic coils 160, liquid embolic 168, occlusion balloon 174 that is detachable, and/or the embolic particles 170 may be delivered to the vessel V to permanently occlude the vessel V. Alternatively, occlusion balloon 174 that is non-detachable, filter 182, bioabsorable agents, or tethered coils may be used to temporarily occlude the vessel V.

After the vessel V has been desirably occluded, the RF generator 6 is operated to deliver ablation energy to the needle electrodes 26 either in a unipolar mode or a bipolar mode. As a result, the treatment region TR is necrosed, thereby creating a lesion on the treatment region TR.

In one preferred method, all of the needle electrodes 26 are used to deliver ablation energy. Alternatively, all of the needle electrodes 26 except the one that was used to deliver the occlusion element are used to deliver ablation energy. In this case, the generator 6 may be configured such that it could allow a user to selectively choose which of the needle electrodes 26 to activate.

Because the vessel V adjacent the treatment region TR is occluded, the probe assembly 4 (or 200) allows ablation of the tissue surrounding the vessel V without substantial heat loss, thereby reducing the possibility of having incomplete necrosis of the tissue surrounding the vessel V. In many cases, a single ablation may be sufficient to create a desired lesion. However, if it is desired to perform further ablation to increase the lesion size or to create lesions at different site(s) within the treatment region TR or elsewhere, the needle electrodes 26 may be introduced and deployed at different target site(s), and the same steps discussed previously may be repeated. When a desired lesion at treatment region TR has been created, the needle electrodes 26 are retracted into the lumen 18 of the cannula 12, and the probe assembly 4 is removed from the treatment region TR.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed:

1. A medical probe assembly for ablating tissue, comprising:
   an elongated shaft having a proximal end and a distal end;
   a handle connected to the proximal end of the elongated shaft and comprising a delivery port;

a plurality of electrodes carried by the elongated shaft, each electrode comprising an electrode lumen; and an indexer configured to selectively place the delivery port in communication with one of the electrode lumens.

2. The medical probe assembly of claim 1, wherein the indexer is rotatable about a longitudinal axis of the elongated shaft.

3. The medical probe assembly of claim 1, wherein the indexer is configured to place the delivery port in direct communication with the selected electrode lumen.

4. The medical probe assembly of claim 1, wherein the indexer is configured to place the delivery port in indirect communication with the selected electrode lumen.

5. A tissue ablation system, comprising:

a probe assembly comprising a plurality of ablation electrodes, each electrode comprising a lumen;

an occlusion element selected from the group consisting of an embolic coil, liquid embolic, an occlusion balloon, embolic particles, and a filter;

an actuator for causing delivery of the occlusion element through a selected electrode lumen; and an indexer configured to place the actuator in communication with a selected electrode lumen.

* * * * *